US009873650B2

(12) United States Patent
Eisaman et al.

(10) Patent No.: US 9,873,650 B2
(45) Date of Patent: Jan. 23, 2018

(54) METHOD FOR EFFICIENT CO2 DEGASIFICATION

(71) Applicant: X Development LLC, Mountain View, CA (US)

(72) Inventors: Matthew D. Eisaman, Port Jefferson, NY (US); Stephen D. Karnitz, Farragut, TN (US); Jessica L. B. Rivest, Palo Alto, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 15/204,315

(22) Filed: Jul. 7, 2016

(65) Prior Publication Data
US 2017/0342006 A1 Nov. 30, 2017

Related U.S. Application Data

(60) Provisional application No. 62/342,061, filed on May 26, 2016.

(51) Int. Cl.
  *C07C 29/151* (2006.01)
  *C25B 1/00* (2006.01)
  (Continued)

(52) U.S. Cl.
  CPC ...... *C07C 29/1516* (2013.01); *B01D 19/0005* (2013.01); *B01D 19/0031* (2013.01);
  (Continued)

(58) Field of Classification Search
  CPC ....... B01D 61/00; B01D 2311/13; C02F 1/20; C02F 2103/08; C02F 2209/06;
  (Continued)

(56) References Cited

U.S. PATENT DOCUMENTS 3,075,828 A   1/1963   Kato et al.
4,036,749 A   7/1977   Anderson
            (Continued)

FOREIGN PATENT DOCUMENTS

CN   102936067 A   2/2013
EP      1276795     3/2006
            (Continued)

OTHER PUBLICATIONS

Willauer, H. D. et al., Extraction of Carbon Dioxide from Seawater by an Electrochemical Acidification Cell. Part 2—Laboratory Scaling Studies, Apr. 2011, 22 pages.
(Continued)

*Primary Examiner* — Jafar Parsa
(74) *Attorney, Agent, or Firm* — Christensen O'Connor Johnson Kindness PLLC

(57) ABSTRACT

A method including acidifying a solution including dissolved inorganic carbon; vacuum stripping a first amount of a carbon dioxide gas from the acidified solution; stripping a second amount of the carbon dioxide gas from the acidified solution; and collecting the first amount and the second amount of the carbon dioxide gas. A system including; a first desorption unit including a first input connected to a dissolved inorganic carbon solution source to and a second input coupled to a vacuum source; and a second desorption unit including a first input coupled to the solution output from the first desorption unit and a second input coupled to a sweep gas source.

19 Claims, 3 Drawing Sheets

(51) Int. Cl.
*B01D 19/00* (2006.01)
*B01D 61/42* (2006.01)
*C01B 31/20* (2006.01)

(52) U.S. Cl.
CPC ............ *B01D 61/422* (2013.01); *C01B 31/20* (2013.01); *C25B 1/00* (2013.01)

(58) Field of Classification Search
CPC ......... Y02C 10/10; C07C 1/20; C07C 29/149; C07C 69/06; C07C 31/04
See application file for complete search history.

(56) References Cited

U.S. PATENT DOCUMENTS

| | | |
|---|---|---|
| 4,392,959 A | 7/1983 | Coillet |
| 4,397,957 A | 8/1983 | Allison |
| 6,402,818 B1* | 6/2002 | Sengupta ............ B01D 19/0031 95/46 |
| 6,905,606 B1 | 6/2005 | Kikuyama et al. |
| 7,117,106 B2 | 10/2006 | Rusta-Sallehy et al. |
| 7,198,722 B2 | 4/2007 | Hussain |
| 7,420,004 B2 | 9/2008 | Hardy et al. |
| 7,655,193 B1 | 2/2010 | Rau et al. |
| 7,700,214 B1 | 4/2010 | Iyer et al. |
| 7,906,028 B2 | 3/2011 | Constantz et al. |
| 7,931,809 B2 | 4/2011 | Constantz et al. |
| 7,947,239 B2 | 5/2011 | Lackner et al. |
| 8,227,127 B2 | 7/2012 | Little et al. |
| 8,313,557 B2 | 11/2012 | Willauer et al. |
| 8,337,589 B2 | 12/2012 | Wright et al. |
| 8,685,250 B2 | 4/2014 | Choi et al. |
| 8,778,156 B2 | 7/2014 | Eisaman et al. |
| 8,784,632 B2 | 7/2014 | Eisaman et al. |
| 8,999,171 B2 | 4/2015 | Wallace |
| 9,227,168 B1 | 1/2016 | DeVaul et al. |
| 2005/0074657 A1 | 4/2005 | Rusta-Sallehy et al. |
| 2008/0033338 A1 | 2/2008 | Smith |
| 2008/0039538 A1* | 2/2008 | Olah ........................ C07C 1/20 518/702 |
| 2008/0093307 A1 | 4/2008 | Somers et al. |
| 2009/0001020 A1 | 1/2009 | Constantz et al. |
| 2010/0028242 A1 | 2/2010 | Willauer et al. |
| 2010/0126180 A1* | 5/2010 | Forsyth ................ F25J 3/04545 60/780 |
| 2010/0233767 A1 | 9/2010 | McMurran |
| 2010/0288700 A1 | 11/2010 | Lahav et al. |
| 2011/0056876 A1 | 3/2011 | Ide et al. |
| 2011/0135551 A1 | 6/2011 | House et al. |
| 2011/0177550 A1 | 7/2011 | McMurran |
| 2011/0206566 A1* | 8/2011 | Stoots ....................... C25B 1/04 422/186.04 |
| 2011/0224578 A1 | 9/2011 | Edman et al. |
| 2011/0226006 A1 | 9/2011 | Lackner et al. |
| 2011/0237839 A1 | 9/2011 | Waldstein |
| 2011/0281959 A1 | 11/2011 | DiMascio et al. |
| 2012/0211421 A1 | 8/2012 | Self et al. |
| 2012/0220019 A1 | 8/2012 | Lackner |
| 2012/0244053 A1 | 9/2012 | Self et al. |
| 2013/0008792 A1 | 1/2013 | Eisaman et al. |
| 2013/0034760 A1 | 2/2013 | Otts et al. |
| 2013/0039837 A1* | 2/2013 | Willauer ................. C01B 31/20 423/438 |
| 2013/0206605 A1 | 8/2013 | DiMascio et al. |
| 2013/0281553 A1 | 10/2013 | Kubic et al. |
| 2013/0343981 A1 | 12/2013 | Wright et al. |
| 2014/0002788 A1 | 1/2014 | Otts et al. |
| 2014/0217024 A1 | 8/2014 | Monzyk et al. |
| 2014/0234735 A1 | 8/2014 | Zhang et al. |
| 2014/0238869 A1 | 8/2014 | DiMascio et al. |
| 2014/0272639 A1 | 9/2014 | Zietlow |
| 2014/0303452 A1 | 10/2014 | Ghaffari |
| 2014/0322803 A1 | 10/2014 | Constantz et al. |
| 2014/0338903 A1 | 11/2014 | Mahmoud et al. |
| 2015/0274536 A1 | 10/2015 | Wright et al. |
| 2015/0298806 A1 | 10/2015 | Lind et al. |
| 2016/0082387 A1 | 3/2016 | Constantz et al. |

FOREIGN PATENT DOCUMENTS

| | | |
|---|---|---|
| EP | 2074066 | 7/2009 |
| EP | 2465600 | 6/2012 |
| EP | 2465601 | 6/2012 |
| EP | 2543427 | 1/2013 |
| WO | WO 90/14877 A1 | 12/1990 |
| WO | WO 9412465 | 6/1994 |
| WO | WO 2010/142943 A2 | 12/2010 |
| WO | WO 2011/090376 A1 | 7/2011 |

OTHER PUBLICATIONS

Eisaman M. D. et al., CO2 extraction from seawater using bipolar membrane electrodialysis, May 2012, 8 pages.
Biorock International Coral Reef Restoration, Biorock International Corporation, 2012, 2 pages.
Rangel C. M. et al., Integrating hydrogen generation and storage in a novel compact electrochemical system based on metal hydrides, Jul. 2008, 5 pages.
U.S. Appl. No. 15/165,867—Method for Feeding Algae Using Reclaimed CO2, filed May 26, 2016, 19 pages.
U.S. Appl. No. 15/165,885—Metal Hydride Electrolysis System, filed May 26, 2016, 21 pages.
U.S. Appl. No. 62/342,065—Chemical Extraction From an Aqueous Solution, filed May 26, 2016, 29 pages.
U.S. Appl. No. 15/165,205—Chemical Extraction From an Aqueous Solution and Power Generator Cooling, filed May 26, 2016, 30 pages.
U.S. Appl. No. 15/165,260—Building Materials From an Aqueous Solution, filed May 26, 2016, 29 pages.
U.S. Appl. No. 15/165,311—Enhanced Hydrocarbon Extraction, filed May 26, 2016, 27 pages.
U.S. Appl. No. 15/165,357—Fuel Synthesis From an Aqueous Solution, filed May 26, 2016, 31 pages.
Eisaman M. D. et al., CO2 separation using bipolar membrane electrodialysis, Energy & Environmental Science, Apr. 2011, 10 pages.
U.S. Appl. No. 14/971,122—Electrodialytic CO2 Purification and Stripping, filed Dec. 16, 2015, 16 pages.
U.S. Appl. No. 14/736,847—Energy Efficient Method for Stripping CO2 From Seawater, filed Jun. 11, 2015, 16 pages.
U.S. Appl. No. 14/750,800—CO2 Sequestration Via Desalination, filed Jun. 25, 2015, 16 pages.
International Search Report and Written Opinion from the International Searching Authority dated Aug. 14, 2017, for International Application No. PCT/US2017/031690, filed May 9, 2017, 12 pages.

* cited by examiner

US 9,873,650 B2

METHOD FOR EFFICIENT CO2 DEGASIFICATION

REFERENCE TO RELATED APPLICATION

This application claims the benefit of U.S. Provisional Application No. 62/342,061 filed on May 26, 2016, the contents of which are incorporated herein by reference.

FIELD

Carbon dioxide separation and collection.

BACKGROUND

The separation of carbon dioxide ($CO_2$) from a mixed-gas source may be accomplished by a capture and regeneration process. More specifically, the process generally includes a selective capture of $CO_2$, by, for example, contacting a mixed-gas source with a solid or liquid adsorber/absorber followed by a generation or desorption of $CO_2$ from the adsorber/absorber. One technique describes the use of bipolar membrane electrodialysis for $CO_2$ extraction/removal from solutions that contain dissolved inorganic carbon (DIC), primarily in the form of carbonate and bicarbonate ions, including seawater, brackish water, desalination brine and sodium/potassium bicarbonate or carbonate solutions.

For capture/regeneration systems, a volume of gas that is processed is generally inversely elated to a concentration of $CO_2$ in the mixed-gas source, adding significant challenges to the separation of $CO_2$ from dilute sources such as the atmosphere. $CO_2$ in the atmosphere, however, establishes equilibrium with the total dissolved inorganic carbon (DIC) in the oceans, which is largely in the form of bicarbonate ions ($HCO_3^-$) at an ocean pH of 8.1-8.3. Therefore, a method for extracting $CO_2$ from the DIC of the oceans would effectively enable the separation of $CO_2$ from atmosphere without the need to process large volumes of air.

A method for extraction of the $CO_2$ from seawater involves conversion of the DIC in seawater (primarily in the form of bicarbonate ion in seawater at its typical pH of 8.3) to dissolved $CO_2$ gas via acidification of the seawater to a pH below 6. Even when all the DIC is converted to $CO_2$ gas, typical DIC concentrations of 2.1 mmol in seawater correspond to an equilibrium partial pressure of the dissolved $CO_2$ gas (assuming all the DIC has been converted to dissolved $CO_2$ gas) of around 0.06 atmospheres (atm) (about 59 mBar) using a Henry's constant for $CO_2$ of about 28.2 atm/M for 20° C. seawater. Assuming that the $CO_2$ gas is dissolved in seawater (total dissolved solids (TDS) of 35,000 mg/L), and using a vapor pressure for 20° C. seawater of 0.023 atm (23 mbar), then an absolute pressure of 0.08 atm (81.8 mbar) must be produced above the seawater solution in order to reach the equilibrium partial pressure for $CO_2$ and begin extracting $CO_2$ gas. As $CO_2$ gas is removed from solution, a concentration of the gas ($CO_2$) decreases and therefore a $CO_2$ equilibrium partial pressure decreases as the extraction proceeds. In order to extract a significant fraction of the dissolved gas, pressures significantly below this value must be achieved. Even if reverse osmosis brine produced in a desalination process is used rather than seawater, the DIC is typically increased by a factor of two, corresponding to an equilibrium partial pressure of 0.14 atm (about 142 mbar). Therefore, in order to extract the dissolved $CO_2$ gas from the acidified seawater, the seawater must be flowed through some sort of degasification device, such as a membrane contactor of a desorption unit. The contactor works by allowing high surface area contact between the solution to be degassed and either a sweep gas or a vacuum with a partial pressure lower than the equilibrium partial pressure of the gas to be extracted. If the $CO_2$ is to be used in subsequent fuel synthesis, fairly pure $CO_2$ is required, eliminating the possibility of using nitrogen or argon sweep gases. Not only does vacuum require substantial energy, but the use of vacuum as a sweep gas also limits the lowest possible pressure to the vapor pressure of water (about 23 mbar (0.023 atm)) in that solution. One drawback of using vacuum can be that as the pressure is lowered to extract a larger fraction of the dissolved $CO_2$, the fraction of water vapor in the extracted gas stream increases.

SUMMARY

A method and system for degassing $CO_2$ from aqueous solutions is disclosed. In one embodiment, a method includes acidifying a solution including dissolved inorganic carbon; vacuum stripping a first amount of the carbon dioxide gas from the acidified solution; after vacuum stripping the first amount of the carbon dioxide gas, stripping a second amount of the carbon dioxide gas from the acidified solution; and collecting the first amount of the carbon dioxide gas and the second amount of the carbon dioxide gas. Instead of a vacuum, the stripping of the second amount of $CO_2$ may be performed with a sweep gas of, for example, carbon monoxide (CO). The collected first and second amounts of $CO_2$ may be combined for subsequent use such as for fuel synthesis. An example of such an application would be the case where $CO_2$ and hydrogen ($H_2$) are concurrently fed to a solid oxide coelectrolysis unit to make syngas which can then be converted into liquid fuels. In syngas production, carbon monoxide (CO) can be included with $CO_2$ as an input to coelectrolysis. Therefore, the presence of CO in the collected $CO_2$ from, from example, seawater or desalination brine (via the sweep gas) may advantageously be used along with the collected $CO_2$ to make syngas. Another example would be the hydrogenation of $CO/CO_2$ mixtures to methanol over transition metal catalysts at elevated temperature and pressure.

In one embodiment, a system includes a first desorption unit including a first input connected to a dissolved inorganic carbon (DIC) solution source and a second input connected to a vacuum source, the first desorption unit operable to remove carbon dioxide gas from a DIC solution and including a solution output; and a second desorption unit including a first input coupled to the solution output from the first desorption unit and a second input coupled to a sweep gas source, the second desorption unit operable to remove carbon dioxide gas from the solution output from the first desorption unit. A collection vessel may be connected to a gas outlet of the first desorption unit and a gas outlet of the second desorption unit to collect and optionally combine $CO_2$ stripped from a solution in the desorption units.

DETAILED DESCRIPTION

Figure 1:
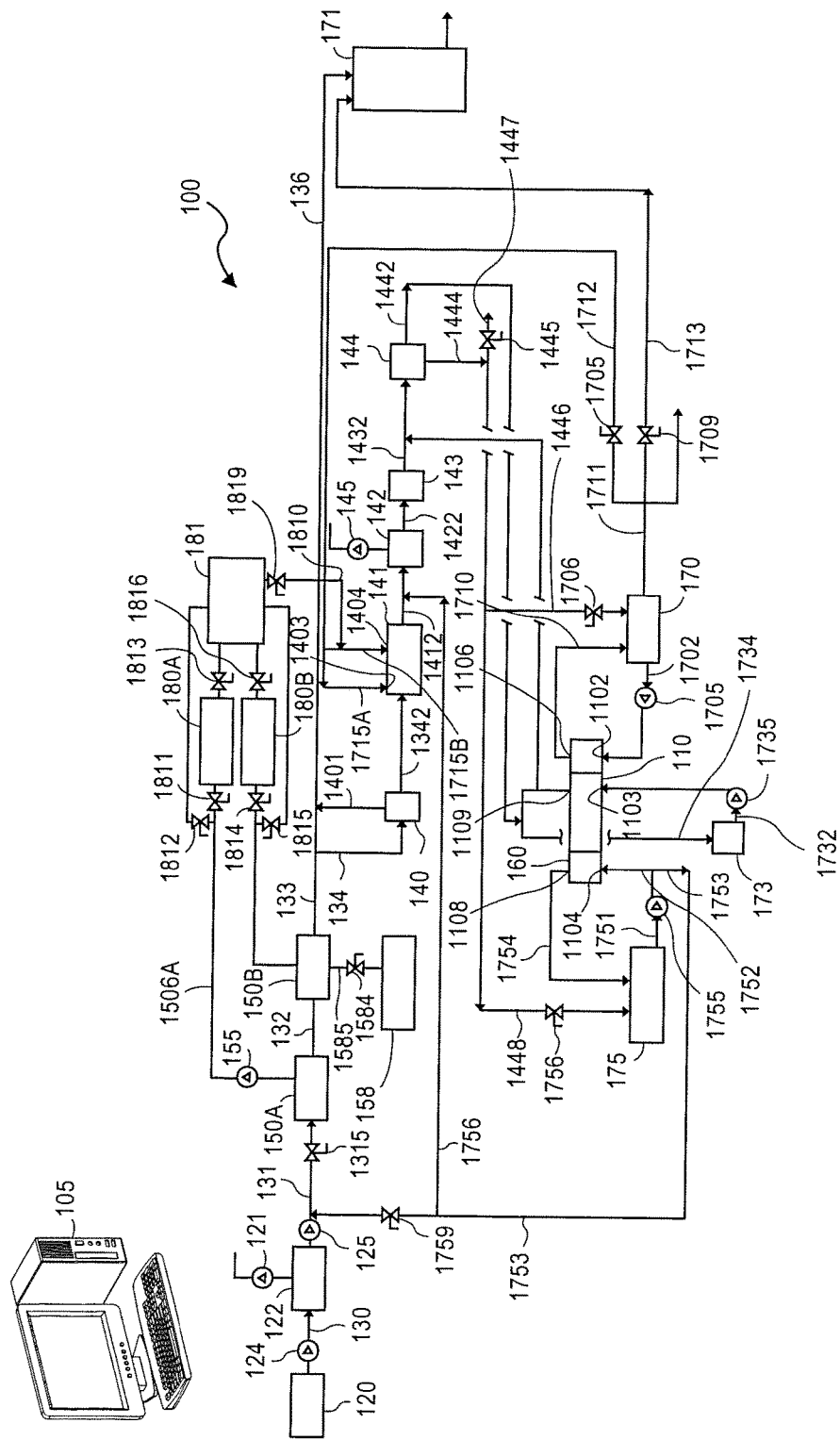
FIG. 1 shows a schematic side view of a system operable to extract (remove) carbon dioxide ($CO_2$) from seawater.

FIG. 1 presents a schematic representation of a system operable to extract/remove $CO_2$ from an aqueous solution such as salt water including but not limited to seawater, brackish water, brine from a desalination or other process or a sodium and/or potassium bicarbonate and/or carbonate solution. An example of seawater will be used in the description of the system and associated processing method, though it is appreciated that the system and associated processing method may be applied to other solutions.

In one embodiment, a method includes acidifying the aqueous solution (e.g., seawater) and then stripping an amount of $CO_2$ gas from the acidified solution with a vacuum followed by stripping an amount of $CO_2$ gas from the acidified solution with a sweep gas. An amount of seawater solution may be acidified by an addition of hydrogen ions to the solution. In one embodiment, an electrodialysis unit such as a bipolar membrane electrodialysis (BPMED) unit may be used to provide an acid solution to seawater to lower a pH of the seawater prior to the stripping of $CO_2$ gas from the seawater. As noted above, seawater of a pH of 8.1 to 8.3 includes dissolved inorganic carbon (DIC). Adding an acid solution to such seawater, in one embodiment, lowers a pH of the seawater solution (acidifying the seawater solution). The DIC, largely in the form of bicarbonate ions ($HCO_3^-$) and carbonate ions ($CO_3^{2-}$) in unacidified pH 8.1 to 8.3 seawater will be converted to dissolved $CO_2$ gas at pH 6 and below. The reactions indicative of $CO_2$ formation in the solution are:

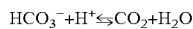

$HCO_3^- + H^+ \leftrightarrows CO_2 + H_2O$

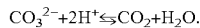

$CO_3^{2-} + 2H^+ \leftrightarrows CO_2 + H_2O.$

In one embodiment, the acidified seawater solution is subjected to a first desorption process wherein a first amount of $CO_2$ is vacuum stripped from the solution. In one embodiment, the vacuum level introduced into a first desorption unit is tuned between 1 atm (1013 mbar) to the vapor pressure of the acidified seawater solution at the temperature of the process. Following the first desorption process, the acidified seawater solution output from the first desorption unit is sent to a second desorption unit and is subjected to a second desorption process where a sweep gas such as carbon monoxide (CO) is used to strip an additional second amount of $CO_2$ from the solution. The first and second amounts of $CO_2$ may be combined for subsequent use or storage.

Referring to FIG. 1, system 100 includes input tank 120 having a volume that is operable to contain a volume of seawater (on the order of pH 8). Input tank 120 is, for example, a stand alone tank, a reservoir, a water mass or an output from an upstream operation (e.g., brine output from a desalination process). In one optional embodiment, seawater from input tank 120 is pumped using pump 124 to desorption unit 122. Desorption unit 122 contains one or more membrane contactors operable to remove, with the aid of vacuum pressure, dissolved oxygen ($O_2$) and nitrogen ($N_2$) in the seawater. FIG. 1 shows vacuum pump 121 to pull a vacuum and extract $O_2$ and $N_2$ from seawater in desorption unit 122. As noted, the presence or use of desorption unit 122 is optional depending on whether it is desired that an ultimate $CO_2$ gas collection be free or at least partially free or substantially free of $O_2$ and $N_2$. If $O_2$ and $N_2$ can be present in the $CO_2$ gas collected according to the method described herein because a use for the $CO_2$ can include the presence of $O_2$ and $N_2$, the desorption unit 122 may be bypassed.

Seawater from input tank 120 or desorption unit 122 is pumped using pump 125 through conduit 131 to desorption unit 150A. In this embodiment, desorption unit 150A is used to extract or remove $CO_2$ gas from seawater. As noted above, one method for extracting $CO_2$ from seawater or other DIC solution is to convert the DIC to dissolved $CO_2$ gas by lowering a pH of the solution (e.g., acidifying the solution). In one embodiment, the seawater is acidified by the addition of an acid solution produced downstream and introduced through conduit 1753 into the seawater in conduit 131 at a point upstream relative to desorption unit 150A. Additional details regarding the acid solution source will be discussed below. The acid solution is added to the seawater prior to the seawater entering desorption unit 150A to lower a pH of (acidify) the seawater entering desorption unit 150A (e.g., lower a pH from about pH 8.1-8.3 to about 6 or lower). In one embodiment, desorption unit 150A includes one or more membrane contactors. A suitable membrane contactor is a Liqui-Cel®X50 fibre type 2.5×8 membrane contactor commercially available from Membrana of Charlotte, N.C. Each membrane contactor has an inlet and an outlet for vacuum and an inlet and an outlet for the liquid solution to allow vacuum stripping of $CO_2$ from the acidified seawater solution. A vacuum level may be tuned between 1 atm and to a vapor pressure of water at the temperature of the process. FIG. 1 shows conduit 131 to deliver acidified seawater to desorption unit 150A with valve 1315 controlling such input and vacuum pump 155 to pull a vacuum and extract/remove $CO_2$ in gaseous form from the seawater. Where $O_2$ and $N_2$ were not previously removed from the seawater (e.g., via desorption unit 122), $CO_2$ gas may be separated from the liquid solution in a gas mixture along with $O_2$ and $N_2$. The vacuum extracted gas is directed to collection vessel 180A through conduit 1506A.

In one embodiment, the seawater solution output from desorption unit 150A is directed to desorption unit 150B through conduit 132. Desorption unit 150B, in one embodiment, is similar to desorption unit 150A and includes one or more membrane contactors (e.g., a Liqui-Cel®X50 fibre type 2.5×8 membrane contactor). Each membrane contactor has an inlet and outlet for a liquid solution (seawater) and a sweep gas, respectively. FIG. 1 shows vessel 158 that contains a sweep gas such as carbon monoxide (CO) or hydrogen. In one embodiment, the sweep gas in vessel 158 is contained under pressure. Vessel 158 provides sweep gas to desorption unit 150B through conduit 1585. The sweep gas, in one embodiment, has a partial pressure of $CO_2$ that is less than a partial pressure of $CO_2$ in the seawater the result of which is the movement of $CO_2$ gas out of the seawater and into the sweep gas. The sweep gas containing $CO_2$ (e.g., a $CO/CO_2$ mixture) is directed to collection vessel 180B. In one embodiment, the gas from desorption unit 150A (extracted via vacuum) and the gas from desorption unit 150B (extracted with a sweep gas) may be combined in collection vessel 181. In another embodiment, the $CO_2$ extracted gases from desorption unit 150A and desorption unit 150B may be directed immediately to collection vessel 181 rather than initially being collected in collection vessel 180A and collection vessel 180B, respectively. FIG. 1 shows valve 1811, valve 1812 and valve 1813 associated with $CO_2$ gas extracted through desorption unit 150A. When valve 1811 in conduit 1506A is open and valve 1812 is closed, the system will allow the $CO_2$ extracted gas to flow into collection vessel 180A. From collection vessel 180A, gas can flow to collection vessel 181 when valve 1813 is open. When valve 1811 is closed and valve 1812 is open, the $CO_2$ extracted gas can flow directly to collection vessel 1181 from desorption unit 150A. FIG. 1 also shows valve 1814, valve 1815 and valve 1816 associated with $CO_2$ gas extracted through desorption unit 150B. When valve 1814 is open and valve 1815 is closed, the system will allow $CO_2$ extracted gas to flow into collection vessel 180B. From collection vessel 180B, gas can flow to collection vessel 181 when valve 1816 is open. When valve 1814 is closed and valve 1815 is open, the $CO_2$ extracted gas can flow directly into collection vessel 181 from desorption unit 150B.

FIG. 1 shows conduit 133 connected to a solution output of desorption unit 150B to carry seawater (e.g., decarbonated, acidified seawater) from the desorption unit. Conduit 133 is divided into conduit 134 and conduit 136. Conduit 134 is used, in one embodiment, to transport a portion of the seawater through processing to convert such seawater to an aqueous sodium chloride (NaCl (aq)) solution as a brine input source for an electrodialysis unit. In one embodiment, conduit 134 is sized to carry a flow rate of liquid that is one to five percent of the flow rate through conduit 133 (a "slip stream"). Conduit 136 is used to, in one embodiment, to transport the seawater (e.g., decarbonated, acidified seawater) to waste tank 171 where it may be neutralized by waste streams associated with the process and, in one embodiment, subsequently released to the ocean.

Referring to that slip stream portion of seawater (e.g., decarbonated seawater) diverted from conduit 133 to conduit 134, FIG. 1 shows conduit 134 connected to a series of processing units intended to collectively convert seawater (e.g., decarbonated seawater) to NaCl (aq). In one embodiment, conduit 133 is connected to nanofiltration unit 140 operable to remove ions and natural organic matter from the seawater. An example of a suitable unit for nanofiltration unit 140 is a nanofiltration unit commercially available from Pure Aqua, Inc. of Santa Ana, Calif. Nanofiltration unit 140 includes a retenate outlet for retenate (organic matter and ions) and a permeate outlet for the seawater that passes through the nanofiltration unit 140. FIG. 1 shows conduit 1401 connected to the retenate outlet. In one embodiment, the retenate is directed to waste tank 171. FIG. 1 shows conduit 1401 connected to conduit 136 to introduce the retenate into the seawater being transported to waste tank 171. In another embodiment, conduit 1401 is connected directly to waste tank 171.

FIG. 1 shows conduit 1342 connected to the permeate output of nanofiltration unit 140. In this embodiment, conduit 1342 is also connected to precipitation unit 141 that is operable to remove calcium and magnesium ions from the seawater (the permeate). In one embodiment, precipitation unit 141 is a tank including input 1403 and input 1404. Where the seawater introduced into precipitation unit 141 is acidic, a base solution is introduced through input 1403 and input 1404 to neutralize the seawater solution in precipitation unit 141. In one embodiment, a base solution is sodium hydroxide (Na(OH) (aq)) that may also be used in an electrodialysis unit associated with system 100 (described below). FIG. 1 shows conduit 1711 connected to an output of tank 170. Tank 170 includes a volume of NaOH (aq). Conduit 1711 is divided into conduit 1712 and conduit 1713. Conduit 1712 is divided into two input conduits into precipitation unit 141 (input conduit 1715A and input conduit 1715B). Valve 1705, in one embodiment, is operable to control a flow of a base solution (e.g., Na(OH) (aq)) through conduit 1711. To precipitate calcium ions and magnesium ions from the seawater as carbonate salts, $CO_2$ gas is also introduced into precipitation unit 141 through input 1404. The $CO_2$ gas may include $CO_2$ gas recovered from desorption unit 150A and/or desorption unit 150B. FIG. 1 representatively shows conduit 1810 connected to an output of vessel 181 and to input conduit 1715B entering precipitation unit at input 1404 (e.g., entering as a sodium carbonate ($Na_2CO_3$) solution).

Conduit 1412 is connected to a solution output of precipitation unit 141. Conduit 1412 is also connected to desorption unit 142 operable to extract/remove $CO_2$ from the solution. Because the solution from precipitation unit 141 was neutralized in the precipitation unit, some of the $CO_2$ in the solution may be dissolved inorganic carbon (DIC). To convert the DIC to $CO_2$, the solution is acidified by introducing an acid source ($H^+$) into the solution. In one embodiment, an acid source to acidify the solution may also provide an acid solution to an electrodialysis unit associated with system 100 (described below). FIG. 1 shows conduit 1756 operable to transport an acid solution, in one embodiment, hydrochloric acid (HCl (aq)), to the solution in conduit 1412 to acidify the solution prior to desorption unit 142. The acidified solution is introduced through conduit 1412 into desorption unit 142. Desorption unit 142 may be similar to desorption units 150A and 150B including one or more membrane. FIG. 1 shows pump 145 connected to desorption unit 142 to pull a vacuum on the unit and remove $CO_2$ from the solution therein.

Connected to a solution output of desorption unit 142 is conduit 1422. In this embodiment, conduit 1422 is connected to resin tower 143. Resin tower 143 is one or more towers operable to remove undesired ions from a solution. In one embodiment, it is desired that the solution recovered from resin tower 143 be exclusively or almost exclusively sodium chloride (NaCl (aq)). Accordingly, the undesired ions removed by subjecting the solution to resin tower 143 are ions other than sodium ions ($Na^+$) and chloride ions ($Cl^-$). An example of a resin tower is an ion exchange resin commercially available from Puretec Industrial Water of Oxnard, Calif.

Connected to a solution output of a permeate of resin tower 143 is conduit 1432. In the embodiment shown in FIG. 1, conduit 1432 is connected to reverse osmosis unit 144. Where the solution form resin tower 143 in conduit 1432 is NaCl (aq), in one embodiment, it is desired to concentrate that solution through the removal of water ($H_2O$) from the solution. Reverse osmosis unit in one embodiment is a unit that removes water from a NaCl (aq) solution. An example of a suitable reverse osmosis unit for reverse osmosis unit 144 is a reverse osmosis unit commercially available from Puretec Industrial Water.

System 100 in the embodiment of FIG. 1 includes electrodialysis unit 110. Electrodialysis unit 110 in this embodiment is a three input/output bipolar membrane electrodialysis unit including base input 1102, brine input 1103 and acid input 1104. FIG. 1 shows tank 170 including a volume of a base solution such as sodium hydroxide (Na(OH) (aq)) and connected via conduit 1702 to base input 1102 to supply a base solution to electrolysis unit 110 using, for example, pump 1705. As noted above, conduit 1710 from tank 170 is divided into conduit 1712 and conduit 1713. Conduit 1713 is operable to supply an amount or volume of the base solution to waste tank 171 to neutralize a solution in waste tank 171. An amount of volume of base solution directed to waste tank 171 may be controlled by valve 1709. FIG. 1 also shows tank 173 including a volume of a brine solution (NaCl (aq)) and connected via conduit 1732 to brine input 1102 to supply a brine solution to electrodialysis unit 110 using, for example, pump 1735. The brine solution is provided to tank 173 through conduit 1442 from reverse osmosis unit 144. FIG. 1 further shows tank 175 including a volume of an acid solution such as hydrochloric acid (HCl (aq)) and connected via conduit 1752 to acid input 1104 to supply an acid solution to electrodialysis unit 110 using, for example, pump 1755.

Figure 2:
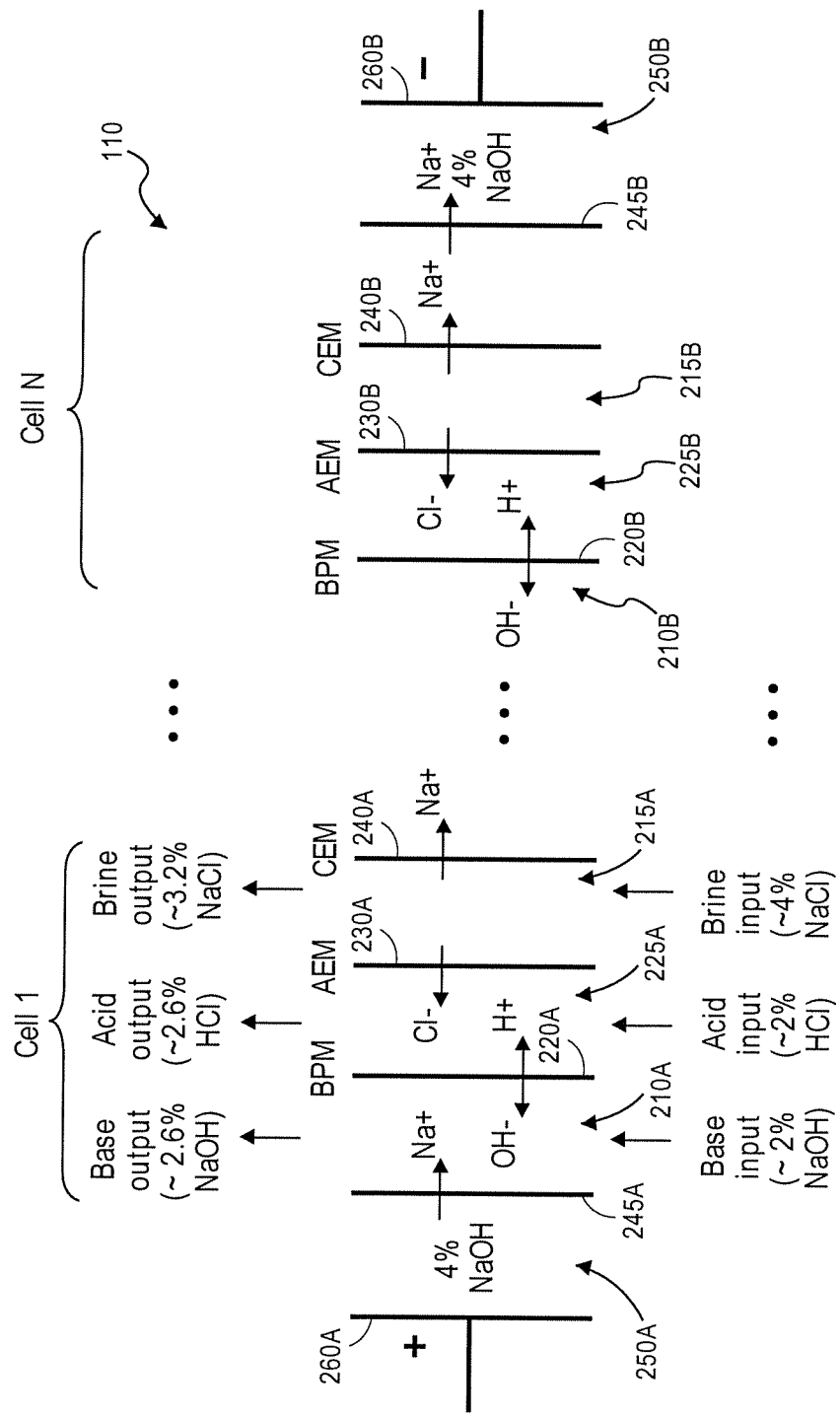
FIG. 2 shows a cross-sectional side view of an embodiment of a bipolar membrane electrodialysis unit in the system of FIG. 1.

FIG. 2 shows a cross-section of an embodiment of electrodialysis unit 110. In this embodiment, the unit representatively consists of several cells in series (e.g., 100 cells, although a membrane stack with a few to a thousand or more cells may be constructed), with each cell including a basified solution compartment (compartments 210A and 210B illustrated); an acidified solution compartment (compartments 210A and 210B illustrated); and a brine solution compartment (compartments 215A and 215B). FIG. 2 also shows a bipolar membrane (BPM) between a basified solution compartment and an acidified solution compartment (BPM 220A and 220B illustrated). A suitable BPM is a Neosepta BP-1E, commercially available from Ameridia Corp. FIG. 2 shows an anion exchange membrane (AEM), such as Neosepta ACS, commercially available from Ameridia Corp. between a brine compartment and an acidified solution compartment (AEM 230A and 230B illustrated); and a cation exchange membrane (CEM) such as Neosepta CMX-S, commercially available from Ameridia Corp. adjacent a brine compartment (CEM 240A and CEM 240B illustrated). Finally, FIG. 2 shows end cap membranes 245A and 245B such as Nafion® membranes that separate the membrane stack from electrode compartment 250A and electrode compartment 250B, respectively. Broadly speaking, under an applied voltage provided to electrodialysis unit 110 of system 100, water dissociation inside the BPM and the ion-selective membranes comprising a BPM will result in the transport of hydrogen ions ($H^+$) from one side of a BPM, and hydroxyl ions ($OH^-$) from the opposite side. AEMs/CEMs, as their names suggest, allow the transport of negatively/positively charged ions through the membrane. The properties of these membranes such as electrical resistance, burst strength, and thickness are provided by the manufacturer (e.g., Neosepta ACS and CMX-S are monovalent-anion and monovalent-cation permselective membranes, respectively). In one embodiment, electrodialysis unit 110 includes electrodes 260A and 260B of, for example, nickel manufactured by De Nora Tech Inc. FIG. 2 shows electrode solution compartment 250A and electrode solution compartment 250B through which, in one embodiment, a NaOH (aq) solution is flowed. Where electrode 260A is a positively-charged electrode, sodium ions (Nat) will be encouraged to move across cap membrane 245A and where electrode 260B is negatively-charged, sodium ions will be attracted to electrode solution compartment 250B. Finally, the solution compartments between adjacent membranes, in one embodiment, are filled with polyethylene mesh spacers (e.g., 762 µm thick polyethylene mesh spacers), and these compartments are sealed against leaks using axial pressure and 794 mm thick EPDM rubber gaskets. In one embodiment, each membrane has a respective active area of 180 $cm^2$.

Referring again to the system illustrated in FIG. 1, there are three outputs from electrodialysis unit 110 base solution output 1106, acid solution output 1108 and brine solution output 1109. FIG. 1 shows base solution output 1106 through which a base solution is discharged (e.g., NaOH). The base solution discharged from base solution output 1106 is returned to tank 170 (a base solution source) through conduit 1710. The discharged base solution is more concentrated than the base solution introduced into electrodialysis unit 110 from tank 170 to be at, for example, a 2 percent concentration. Representatively, a base solution of NaOH (aq) is introduced to electrodialysis unit 110 at a 2 percent concentration and discharged at a 2.6 percent concentration. To control a concentration of NaOH (aq) in tank 170, water is introduced into the tank. FIG. 1 shows conduit 1444 connected to reverse osmosis unit 144 to transport a permeate (water) to tank 170 and tank 175. Conduit 1444 is divided into conduit 1446 connected to tank 170 and conduit 1448 connected to tank 175. An amount or volume of water introduced into tank 170 may be controlled by valve 1706 in conduit 1446. Excess permeate (water) is directed to conduit 1447 to waste through valve 1447.

FIG. 1 shows acid solution output 1108 of electrodialysis unit 110 through which an acid solution is discharged (e.g., HCl). The acid solution discharged through acid solution output 1108 is directed to tank 175 (an acid solution source) through conduit 1754. The discharged acid solution is more concentration than the acid solution introduced into electrodialysis unit 110 from tank 175. Representatively, an acid solution of HCl is introduced into electrodialysis unit at 2 percent and is discharged from the unit at 2.6 percent. To control a concentration of HCl in tank 175 (to maintain a 2 percent concentration for input to electrodialysis unit), water is added to tank 175. FIG. 1 shows conduit 1448 connected to tank 175 to bring water to tank 175 from reverse osmosis unit 144. An amount or volume of water introduced into tank 175 may be controlled by valve 1756 in conduit 1448.

FIG. 1 further shows brine solution output 1109 of electrodialysis unit 110 through which a brine solution is discharged (NaCl (aq)). The brine solution discharged through brine solution output 1109 is returned to tank 173 through conduit 1734.

To extract/remove $CO_2$ from seawater, a portion of the acid solution in tank 175 (e.g., a 2 percent HCl solution) is directed through conduit 1753 to, in this embodiment, be introduced into a seawater solution discharged from desorption unit 122. FIG. 1 shows conduit 1753 connecting with conduit 131 between desorption unit 122 and desorption unit 150A. Acidifying the seawater, in one embodiment, comprises reducing a pH of the seawater in conduit 131 to a pH that promotes a conversion of DIC in the seawater solution to $CO_2$ (e.g., dissolved $CO_2$). In an embodiment where a pH of seawater discharged from desorption unit 122 is on the order of pH 8.1-8.3, acidifying the seawater by the introduction of an acid solution through conduit 1753 comprises reducing a pH of the seawater in conduit 131 (upstream of desorption unit 150A) to around pH 6 or lower.

In one embodiment, an operation of system 100 described above may be controlled by a controller. FIG. 1 shows controller 105 that may be connected through wires or wirelessly to various units of system 100 such as pump 124 to transfer seawater from input tank 120 to desorption unit 122; vacuum pump 121 to extract $O_2$ and $N_2$ from desorption unit 122; pump 125 to transfer seawater into desorption unit 150A; vacuum pump 145 to extract $CO_2$ from desorption unit 145; pump 1725 to introduce a base solution from tank 170 into electrodialysis unit 110; pump 1755 to introduce an acid solution into electrodialysis unit 110; and pump 1735 to introduce brine solution into electrodialysis unit 110 from tank 173. Variable pumps (IDNM 3534 motor and VS1MX Microdrive, Baldor Electric Company) can be used to control the flow rate and pressure of seawater and electrode solution. It is appreciated that the described pumps are representative of pumps to operate the system as described. In other embodiments, fewer or additional pumps may be utilized. In addition to the described pumps, in one embodiment, controller 105 is connected to various valves to control the flow of liquids and gases through the system. Representatively, controller 105 is connected to valve 1315 to control a flow of acidified seawater into desorption unit 150A; valve 1584 to control a flow of a sweep gas into desorption unit 150B; valves 1811, 1812 and 1813 to control a flow of $CO_2$ gas extracted through first desorption unit 150A into collection vessel 180A and/or collection vessel 181; valves 1814, 1815 and 1816 to control a flow of $CO_2$ gas extracted through desorption unit 150B into collection vessel 180B and/or collection vessel 181; valve 1706 to control a flow of water from reverse osmosis unit 144 into tank 170; valve 1756 to control a flow of water into tank 175; valve 1819 to control of $CO_2$ gas from collection vessel 181 into conduit 1715B connected to precipitation unit 141; valve 1445 to control a flow of water from reverse osmosis unit 144 to waste; valve 1705 to control a flow of a base solution from tank 170 to waste tank 171; and valve 1759 to control a flow of an acid solution added to seawater in conduit 131. It is appreciated that the described valves are representative of valves that may be present in system 100 and controlled by controller 105 to operate the system. In other embodiments, additional or fewer valves may be present and controlled by controller 105.

Figure 3:
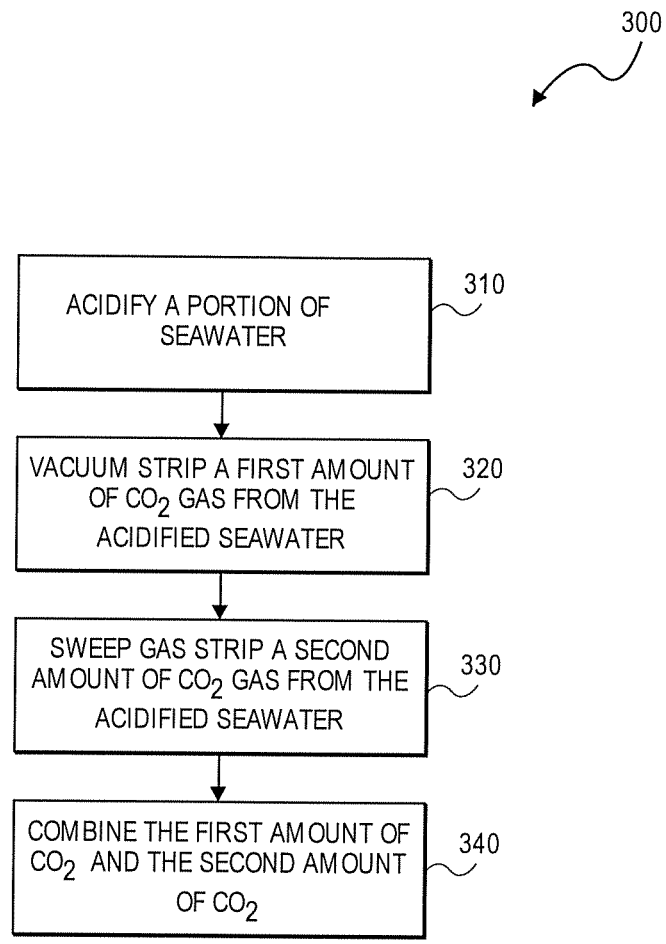
FIG. 3 presents a flow chart of a representative method of extracting $CO_2$ from seawater.

In one embodiment, controller 105 contains machine-readable program instructions as a form of non-transitory media. In one embodiment, the program instructions perform a method of extracting and collecting $CO_2$ from seawater. FIG. 3 presents a flow chart of a representative method. The program instructions associated with controller 105 direct, for example, the optional scrubbing of the seawater to remove $O_2$ and $N_2$ in desorption unit 122 through the operation of pump 124 to transfer seawater from input tank 120 to desorption unit 122 and the operation of pump 121 to pull a vacuum in the desorption unit. Referring to FIG. 3, the program instructions also direct the acidifying of the seawater through control of valve 1759 in conduit 1753 and the operation of pump 1755 to transfer an acid solution from tank 175 (FIG. 3, block 310). The acidified seawater is directed to a first desorption unit where $CO_2$ is extracted/separated by vacuum stripping and subsequently collected, optionally, in a mixture with oxygen and nitrogen (FIG. 3, block 320). With reference to system 100 of FIG. 1, the program instructions direct the operation of valve 1315 to allow acidified seawater to enter desorption unit 150A and pump 155 to pull a vacuum in the desorption unit. The program instructions also direct the $CO_2$ extracted through desorption unit 150A into collection vessel 180A by controlling valves 1811 and 1812. The acidified seawater from desorption unit 150A is directed to desorption unit 150B where $CO_2$ is extracted/separated and subsequently collected (FIG. 3, block 330). With reference to system 100 in FIG. 1, the program instructions direct the operation of valves 1584 to introduce a sweep gas into desorption unit 150B and of valves 1814, 1815 and 1816 to direct extracted/separated $CO_2$ gas through the desorption unit into vessel 180. Finally, the program instructions direct the combination of the $CO_2$ extracted/separated by vacuum stripping and the $CO_2$ extracted/separated by sweep gas stripping (FIG. 3, block 340). With reference to system 100 in FIG. 1, in one embodiment, the program instructions direct the operation of valves 1813 and 1816 to direct the $CO_2$ gas into collection vessel 181. In another embodiment, the program instructions direct the direct transfer of extracted/separated $CO_2$ gas from desorption unit 150A and desorption unit 150B, respectively, by controlling valves 1811 and 1812 and valves 1814 and 1815.

In one embodiment, controller 105 also regulates and monitors the system. Such regulation and monitoring may be accomplished by a number of sensors throughout the system that either send signals to controller 105 or are queried by controller 105. For example, with reference to electrodialysis unit 110, such monitors may include one or more pH gauges to monitor a pH within the units as well as pressure sensors to monitor a pressure among the compartments in electrodialysis unit 110 is to avoid mechanical damage to the electrodialysis membrane stack and the unwanted mixing of different solution streams within the membrane stack. Other monitors include one or pressure monitors associated with electrodialysis unit 110 to minimize the expulsion of gases within the unit. Concentration monitors may also be present to measure a concentration of a base solution in tank 170 and an acid solution in tank 175. Still further flow rate monitors and pH may be present in conduit 1753 and conduit 131 to monitor a flow and a pH of an acid solution and seawater, respectively.

Described is a two-stage process for $CO_2$ degasification, where the first stage includes feeding the acidified seawater into a membrane contactor and using vacuum to extract pure $CO_2$. The vacuum level may be tuned anywhere between 1 atm to the vapor pressure of water at the temperature of the process. In a case where only a vacuum membrane contactor was used, the extracted $CO_2$ percentage would be limited by the vapor pressure of water and the increasing amount of water vapor extracted at lower pressures. In the described two-stage process, a second membrane contactor stage is added, where the output seawater solution of the membrane contactor in the stage that uses vacuum is fed into a second stage membrane contactor that uses a sweep gas such as CO. In one embodiment, this second stage is able to remove as much of the remaining $CO_2$ as is desired.

Using the case of seawater where practicalities of vacuum pump pressures and water vapor content limits extraction efficiency of $CO_2$ at an absolute pressure of 35 mbar (0.034 atm) to 80 percent, half of the remaining unextracted 20 percent of dissolved $CO_2$ could be extracted in the second stage contactor using CO as a sweep gas, resulting in a total $CO_2$ removal efficiency of 90 percent and a gas mixture from the second contactor of 0.06 percent $CO_2$ and 99.4 percent CO (since a partial pressure of 0.06 atm $CO_2$ would be required to extract 90 percent of the $CO_2$ from the seawater). The extraction of efficiency in stage one and stage two can be selected for a given application by adjusting a vacuum level in stage one and a sweep gas flow rate in stage two of 80 percent at stage one extraction and a total extraction of 90 percent. In another embodiment, 50 percent of the $CO_2$ in a solution is extracted in stage one and 80 percent of the remaining 50 percent in stage two to achieve the same total $CO_2$ extraction efficiency of 90 percent.

After extraction, the outputs from stage one and stage two can be directly mixed and then used as input for fuel synthesis, or the stage two $CO/CO_2$ stream can be first sent through a system to separate the CO and $CO_2$, and then any custom fraction of CO and $CO_2$ can be mixed for input into a fuel synthesis step.

The above-described system may be used to collect $CO_2$ from seawater or any other liquid source. Such collection may serve to reduce a concentration of $CO_2$ in the atmosphere and also provide a source of $CO_2$ may be used in various industries, including, but not limited to, as a fuel source. Representatively, collected $CO_2$ via the above-described extraction process may be concurrently fed with hydrogen to a solid oxide coelectrolysis unit to make syngas which can then be converted into liquid fuels. In syngas production, carbon monoxide (CO) can be included with $CO_2$ as an input to coelectrolysis. Therefore, the presence of CO in the collected $CO_2$ via a sweep gas desorption may advantageously be used along with the collected $CO_2$ to make syngas. Another example would be the hydrogenation of $CO/CO_2$ mixtures to methanol over transition metal catalysts at elevated temperature and pressure.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   acidifying a solution including dissolved inorganic carbon with aqueous HCl from an electrodialysis unit to form an acidified solution, wherein the electrodialysis unit receives a salt water solution and outputs the aqueous HCl and aqueous NaOH;
   converting the dissolved inorganic carbon into carbon dioxide gas in response to acidifying the solution with the aqueous HCl from the electrodialysis unit;
   vacuum stripping a first amount of the carbon dioxide gas from the acidified solution;
   after vacuum stripping the first amount of the carbon dioxide gas, stripping a second amount of the carbon dioxide gas from the acidified solution; and
   collecting the first amount of the carbon dioxide gas and the second amount of the carbon dioxide gas.

2. The method of claim 1, wherein collecting the first amount of the carbon dioxide gas and the second amount of the carbon dioxide gas comprises combining the first amount of the carbon dioxide gas and the second amount of the carbon dioxide gas.

3. The method of claim 1, wherein the solution comprises sea water.

4. The method of claim 1, wherein vacuum stripping comprises passing the acidified solution through a membrane contactor in the presence of a vacuum.

5. The method of claim 4, wherein stripping a second amount of the carbon dioxide gas comprises passing the acidified solution through a second membrane contactor in the presence of a sweep gas, wherein the second membrane contactor is coupled to receive the acidified solution from the first membrane contactor.

6. The method of claim 5, wherein the sweep gas comprises a partial pressure of carbon dioxide gas that is less than a partial pressure of carbon dioxide gas in the acidified solution.

7. The method of claim 5, wherein the sweep gas comprises at least one of carbon monoxide or hydrogen.

8. The method of claim 7, wherein collecting the first amount of the carbon dioxide gas and the second amount of the carbon dioxide gas comprises combining the first amount of the carbon dioxide gas and the second amount of the carbon dioxide gas and the combination includes an amount of the sweep gas.

9. The method of claim 7, wherein collecting the second amount of carbon dioxide comprises collecting an amount of the sweep gas, the method further comprising separating the carbon dioxide from an amount of the sweep gas.

10. The method of claim 1, wherein the collected first amount of carbon dioxide and second amount of carbon dioxide are electrolyzed with steam.

11. The method of claim 1, further comprising hydrogenating the collected first amount of carbon dioxide and second amount of carbon dioxide to methanol.

12. The method of claim 3, further comprising:
    filtering the sea water with a nanofiltration unit to remove ions and organic matter from the sea water; and
    removing calcium and magnesium ions from the seawater using a precipitation unit coupled to receive the seawater from the nanofiltration unit, and coupled to receive the aqueous NaOH from the electrodialysis unit, wherein the salt water includes the sea water.

13. The method of claim 1, wherein the electrodialysis unit is coupled to perform operations comprising:
    receiving the salt water solution with a brine solution compartment disposed in the electrodialysis unit;
    applying a voltage across electrodes in the electrodialysis unit;
    outputting the saltwater solution from the brine solution compartment with a lower salt concentration in response to the voltage applied across the electrodes;
    receiving the aqueous HCl with an acidified solution compartment disposed in the electrodialysis unit;
    applying the voltage across the electrodes in the electrodialysis unit; and
    outputting the aqueous HCl, with a higher HCl concentration, from the acidified solution compartment to acidify the solution, wherein chlorine ions in the brine solution compartment traveled to the acidified solution compartment in response to the voltage across the electrodes.

14. The method of claim 13, wherein the electrodialysis unit is coupled to perform operations further comprising:
    receiving the aqueous NaOH with a basified solution compartment disposed in the electrodialysis unit;
    applying the voltage across the electrodes in the electrodialysis unit; and
    outputting the aqueous NaOH from the basified solution compartment with a higher NaOH concentration in response to the voltage applied across the electrodes.

15. The method of claim 14, wherein in response to the voltage, the chlorine ions flow through an anion exchange membrane disposed between the brine solution compartment and the acidified solution compartment, and wherein in response to the voltage, hydrogen ions and hydroxyl ions flow through a bipolar membrane disposed between the acidified solution compartment and the basified solution compartment.

16. The method of claim 15, wherein applying the voltage across the electrodes in the electrodialysis unit includes collecting sodium ions at a negatively charged terminal, and wherein the brine solution compartment, the acidified solution compartment, and the basified solution compartment are included in a first cell in a plurality of cells in the electrodialysis unit.

17. The method of claim 13, further comprising neutralizing the acidified solution with the aqueous NaOH output from the basified solution compartment in the electrodialysis unit, after stripping a second amount of the carbon dioxide gas from the acidified solution.

18. The method of claim 1, further comprising:
removing ions from the solution with a resin tower; and
outputting the salt water solution from the resin tower to the electrodialysis unit.

19. The method of claim 18, further comprising removing water from the salt water with a reverse osmosis unit coupled between the resin tower and the electrodialysis unit.

* * * * *